United States Patent [19]

Pfeifer et al.

[11] Patent Number: 5,779,689
[45] Date of Patent: Jul. 14, 1998

[54] DIAPERS WITH ELASTICIZED CROTCH AND END REGIONS AND A PROCESS AND APPARATUS FOR THE CONTINUOUS MANUFACTURE THEREOF

[75] Inventors: Roland Pfeifer, Bondues, France; Joakim Berntsson, Onsala, Sweden

[73] Assignee: Peaudouce, Linselles, France

[21] Appl. No.: 563,737

[22] Filed: Nov. 28, 1995

Related U.S. Application Data

[63] Continuation of Ser. No. 39,479, filed as PCT/FR91/00830, published as WO92/07531, May 14, 1992, abandoned.

[30] Foreign Application Priority Data

Oct. 26, 1990 [FR] France ................... 90 13268

[51] Int. Cl.⁶ .................. A61F 13/15; B32B 31/00
[52] U.S. Cl. ................ 604/385.2; 601/344; 156/41; 156/164; 156/163
[58] Field of Search ............... 604/385.1, 385.2, 604/393, 394, 395, 396, 397, 398; 156/163, 494–496, 164

[56] References Cited

U.S. PATENT DOCUMENTS

| | | |
|---|---|---|
| 4,022,456 | 5/1977 | Hooper et al. |
| 4,353,762 | 10/1982 | Bouda ................ 156/164 |
| 4,402,688 | 9/1983 | Julemont ............. 604/385.2 |
| 4,618,384 | 10/1986 | Sabee ................. 156/205 |
| 4,675,068 | 6/1987 | Lundmark ............ 156/164 |
| 4,718,901 | 1/1988 | Singheimer ......... 604/385.2 |
| 4,725,468 | 2/1988 | McIntyre ............ 604/385.2 |
| 4,726,873 | 2/1988 | Ales et al. ........... 156/495 |
| 4,762,582 | 8/1988 | de Jonckheere ..... 156/164 |
| 4,915,767 | 4/1990 | Ragala et al. ........ 156/164 |
| 4,917,746 | 4/1990 | Kons et al. .......... 156/164 |

FOREIGN PATENT DOCUMENTS

| | | |
|---|---|---|
| A1 0048010 | 3/1982 | European Pat. Off. |
| A1 0048011 | 3/1982 | European Pat. Off. |
| A1 0121178 | 10/1984 | European Pat. Off. |
| 0170922 | 2/1986 | European Pat. Off. |
| B1 0229753 | 10/1989 | European Pat. Off. |
| 0563971 | 10/1993 | European Pat. Off. ... 601/385.2 |
| 2542979 | 9/1984 | France. |
| 3613086 A1 | of 1987 | Germany. |
| 2173689 | 10/1986 | United Kingdom. |
| 2248380 | 4/1992 | United Kingdom ... 604/385.2 |

*Primary Examiner*—John G. Weiss
*Assistant Examiner*—K. M. Reichle
*Attorney, Agent, or Firm*—Burns, Doane, Swecker & Mathis, L.L.P.

[57] ABSTRACT

A disposable diaper comprises a liquid-impervious outer sheet (2), defining a narrower crotch region (27) between two wider end or belt regions (28, 29), an absorbent pad (22), fastening members (24) for closing the diapers, and elastic members (4) attached under tension to the impervious sheet (2) on both sides of the absorbent pad (22), substantially over the whole length of the impervious sheet, with a higher tension in the crotch region (27) than in the end regions (28, 29), having, in the two end regions (28, 29), sections (4c) converging in the direction of the transverse edges of the impervious sheet, so that the elastic members (4) form an elastic barrier which practically surrounds the absorbent pad (22) and provide the impervious sheet both with a lengthwise elasticity in the crotch region and a transverse elasticity in the end regions.

18 Claims, 8 Drawing Sheets

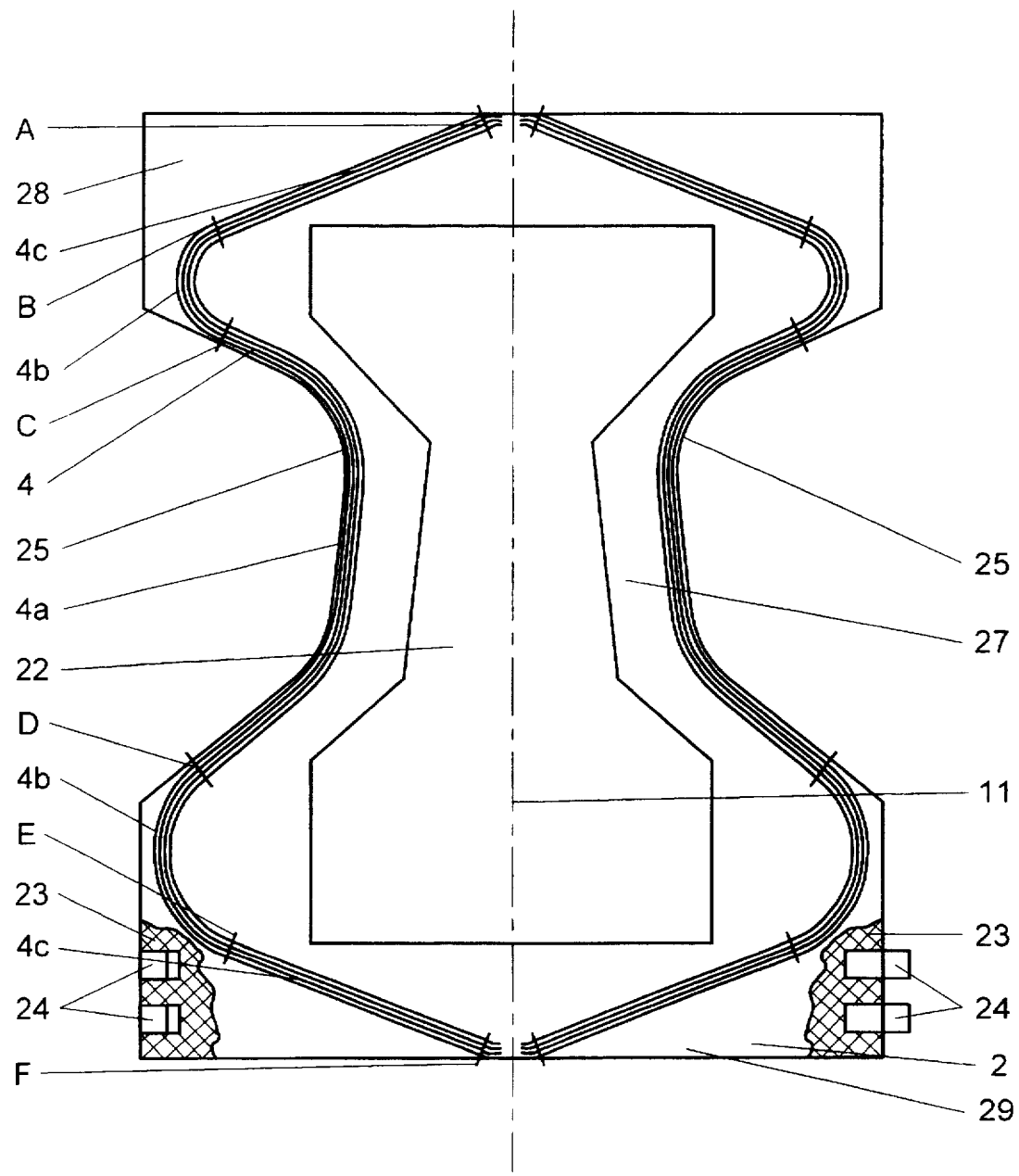

DIAPERS WITH ELASTICIZED CROTCH AND END REGIONS AND A PROCESS AND APPARATUS FOR THE CONTINUOUS MANUFACTURE THEREOF

This application is a continuation of application Ser. No. 08/039,479, filed as PCT/FR91/00830, Oct. 22, 1991 published as WO92/07531, May 14, 1992, now abandoned.

The present invention relates to disposable diapers and to a process and apparatus for the continuous manufacture thereof.

BACKGROUND OF THE INVENTION

Disposable diapers, which can be employed for young children or for incontinent adults usually comprise a liquid-impervious outer sheet, and a liquid-permeable inner sheet, the two sheets being of a substantially rectangular overall shape. Preferably median indentations are cut out in the lengthwise edges of the sheets for allowing legs to pass through and which define in the lengthwise direction of the diapers a narrower crotch region between two wider end regions. In addition, these diapers comprise an absorbent pad whose dimensions are smaller than those of the said two sheets. This absorbent pad is arranged between the said sheets so that its edges are set back in relation to the corresponding edges of the two sheets. The two sheets are joined together by adhesive bonding along their edges, around the absorbent pad. Furthermore, these diapers comprise fastening members for closing the diapers, using the two end regions, around a user's waist. These fastenings may be, for example, adhesive fastenings arranged on the lengthwise edges of the sheets, preferably in the vicinity of the transverse edge of the end region forming the rear part of the diapers.

In order to improve the sealing of the diapers around the user's legs in the crotch region, it is known, furthermore, to provide on such diapers in said crotch region elastic members adhesively bonded under tension to the inner face of the impervious outer sheet, on each side of the absorbent pad, along each of the said indentations.

These elastic members in said crotch region are generally rectilinear, but it has also been proposed in Patent Application EP-A-048,010 to attach these elastic members in a curved form to allow them to follow the shape of the indentation. According to this document, the elastic members are attached under tension to the impervious sheet solely in the crotch region.

It has furthermore been proposed by Patent Application FR-A-2,542,979 to attach such lengthwise elastic members under variable tension to a diaper over the whole length thereof, namely under high tension and in a curved form in the crotch region and under a lower tension in the end regions.

Furthermore, according to Patent Application EP-A-229, 753, lengthwise elastic members of a rectilinear form are attached under a high tension in the crotch region of a diaper for incontinent individuals and are, furthermore, attached under a lower tension and following a diverging or a diverging and then converging path in the end regions of the diapers. According to this document, the diverging and/or converging sections of the elastic members are inclined at an angle of the order of 30° in relation to the lengthwise direction of the diapers. These elastic members improve the lateral sealing of the diaper but do not contribute in any way to the improvement of sealing in the lengthwise direction (where the belt is).

Finally, Patent Application GB-A-2,173,689 discloses diapers comprising both lengthwise elastic members extending throughout the length of the diaper, along both lengthwise edges of the absorbent pad, and transverse elastic members extending throughout the width of the diaper in the two end regions. The main disadvantage when using these two type of elastic members consists in difficulties for the continuous manufacturing of such diapers when the elastic members must be attached in a stretched state to the impervious sheet. In fact, such diapers are manufactured continuously, either in the lengthwise direction or in the transverse direction, from a continuous strip of impervious sheet onto which either the lengthwise elastic members or the transverse elastic members are attached continuously in a stretched state. On the other hand, the attachment under tension of other elastic members extending perpendicularly to the direction of manufacture cannot be done continuously and this considerably limits the rate of manufacture. In addition, the use of two lengthwise elastic members and of two transverse elastic members on each diaper increases the cost of the diapers.

SUMMARY OF THE INVENTION

The present invention relates to a diaper which, while being simple and inexpensive to manufacture, ensures good leakproofing both in the crotch region and in the end regions. Another object of the invention is a process for the continuous manufacture of such diapers, which is particularly simple and which permits particularly high rates of manufacture. A further object of the invention is an apparatus for implementing this process, designed so as to permit, on the one hand, a high rate of manufacture and, on the other hand, a particularly accurate placing of the elastic members.

The disposable diapers in accordance with the invention comprise a liquid-impervious outer sheet, a liquid-permeable inner sheet, the two sheets being of a substantially rectangular overall shape. Median indentations are cut out from their lengthwise edges for allowing legs to pass through and defining in the lengthwise direction of the diapers a narrower crotch region between two wider end regions. The diapers additionally comprise an absorbent pad whose dimensions are smaller than those of the two sheets and which is arranged between the said two sheets so that its edges are set back in relation to the corresponding edges of the two sheets. The two sheets are joined together by adhesive bonding at their edges, around the absorbent pad. The diapers comprise, furthermore, fastening members for closing the diapers, using the two end regions, around a user's waist. Finally, the diapers comprise elastic members attached under tension by adhesive bonding to the inner face of the impervious sheet along both lengthwise edges of the absorbent pad, substantially over the whole length of the impervious sheet, with a higher tension in the crotch region than in the end regions. According to the invention the elastic members arranged on the opposite lengthwise edges of the absorbent pad have, in the two end regions, sections converging in the direction of the transverse edges of the impervious sheet, so that the elastic members form an elastic barrier which practically surrounds the absorbent pad and provide the impervious sheet both with a lengthwise elasticity in the crotch region and a transverse elasticity in the end regions.

With the diapers in accordance with the invention it is therefore possible to obtain, by means of only two elastic members, a result equivalent to that obtained hitherto using four elastic members.

The converging sections of the elastic members preferably follow a substantially rectilinear path and are inclined by at least 45° and preferably at least 60° in relation to the lengthwise direction of the diapers.

Furthermore, the length of the converging sections of the elastic members is preferably such that the length of the projections of the said sections onto the transverse edges of the diaper correspond to at least 40% and preferably to more than 50% of the length of the said transverse edges of the diapers.

Furthermore, in the diapers in accordance with the invention, the converging sections of the two elastic members join together or approach each other as closely as possible near each transverse edge of the diapers. The maximum distance separating the two elastic members at or near the transverse edges of the diaper corresponds to less than 20% and preferably to less than 15% of the length of the said edges, that is to say of the width of the diapers at the transverse edges thereof. Depending on the shape of the absorbent pad, this distance is also less than 50% and preferably less than 30% of the maximum width of the absorbent pad.

In the converging sections, the elastic members advantageously have a tension which is at least 50% lower than the tension of the elastic members in the crotch region.

In the case of diapers comprising an absorbent pad which is, just like the two sheets, hourglass-shaped, that is to say of a rectangular overall shape with two opposite lengthwise indentations in the crotch region, it is advantageous that each of the elastic members is comprised of, in the median part of the crotch region, substantially rectilinear sections followed on both sides by outwardly concave curved sections, themselves followed in the end regions by outwardly convex curved sections to which the said converging sections are joined. In this case, the said outwardly convex sections advantageously have a lower tension than the converging sections, themselves having a lower tension than the tension of the elastic members in the crotch region.

Thus, the elastic members may be, for example, extended between approximately 100 and 200% in the crotch region, between approximately 5 and 10% in the outwardly convex sections and between approximately 40 and 60% in the converging sections.

Within the scope of the invention each elastic member may either consist of an elastic strand or comprise a plurality of individual elastic strands arranged parallel to each other.

Following the process in accordance with the invention for the continuous manufacture of such diapers, a continuous impervious sheet is passed over a supporting and driving member. To attach the elastic members by adhesive bonding onto the said sheet, continuous elastic members are brought into contact with the said sheet, on the said supporting and driving member, while varying at regular intervals the tension of the said elastic members at their points of contact with the said sheet. The said points of contact are displaced at regular intervals transversely to the lengthwise direction of the said sheet so as to attach the said elastic members by adhesive bonding onto the said sheet so that the said elastic members form, on the said sheet, two repetitive continuous outlines which are symmetrical in relation to the lengthwise axis of the sheet. According to the invention, the transverse displacement, at regular intervals, of the points of contact between the elastic members and the impervious sheet is controlled so that the said two outlines cross each other at regular intervals or come close to the point of touching each other or nearly touching each other.

To simplify the manufacture it is advantageous not to apply adhesive to the elastic members but to apply adhesive to the impervious sheet on its face receiving the elastic members, for subsequent adhesive bonding of the said elastic members onto the sheet.

In order to allow a retraction of the ends of the elastic members when the impervious sheet and the elastic members adhesively bonded thereon are subsequently transversely cut, there may be left, in the middle of the width of the impervious sheet during the application of the adhesive, an adhesive-free strip.

For the same purpose, it is possible to intermittently interrupt the application of adhesive onto the impervious sheet in a region situated in the middle of the width of the said sheet, so as to form at regular intervals an adhesive-free window at the emplacement where the paths of the elastic members cross or touch each other.

Still for the same purpose, it is also possible to apply adhesive to the impervious sheet continuously over its whole width and to spray an antiadhesive material at regular intervals onto the elastic members.

The apparatus for the continuous manufacture of diapers in accordance with the present invention comprises, for the accurate guidance of each elastic member, a guiding means for receiving the elastic members mounted in the immediate proximity of the supporting and driving member over which the impervious sheet passes, preferably by means of a frictionless bearing, on a trolley driven in translation transversely to the direction of movement of the supporting and driving member, so that it can be freely oriented about an axis substantially perpendicular to the surface of said guiding and driving means. This trolley may be driven by a linear or rotary motor, preferably controlled, with index-linking to the movement of the supporting and driving member, by an electronic control unit commanded by a computer.

The guiding means may advantageously comprise a guiding head with closed holding means for the elastic members, for example in the form of parallel drilled holes or channels through which the elastic members are threaded, so that escaping of the elastic members from the holding means during the translational movements of the guiding means is prevented.

Furthermore, the variable stretching tensions of the elastic members may be produced by rotary feeding instruments which exert a clamping effect on the elastic members and whose variable-speed drive is controlled by the same computer-commanded electronic control unit.

The trajectories for positioning the elastic members on the impervious sheet may be preferably designed and controlled by a computer program, as can the shape of the indentations cut out in the crotch region of the impervious sheet, for example by a device incorporating water jets, permitting an accurate adjustment of the outer edge of the elastic members in relation to the edge of the indentations.

A number of illustrative embodiments of the invention will be described below in greater detail with reference to the attached drawings and without any limitation being implied.

BRIEF DESCRIPTION OF THE DRAWING FIGURES

FIG. 5a is a top view, with partial cutaway, of a diaper manufactured according to FIG. 4;

DETAILED DESCRIPTION OF THE INVENTION

Figure 1:
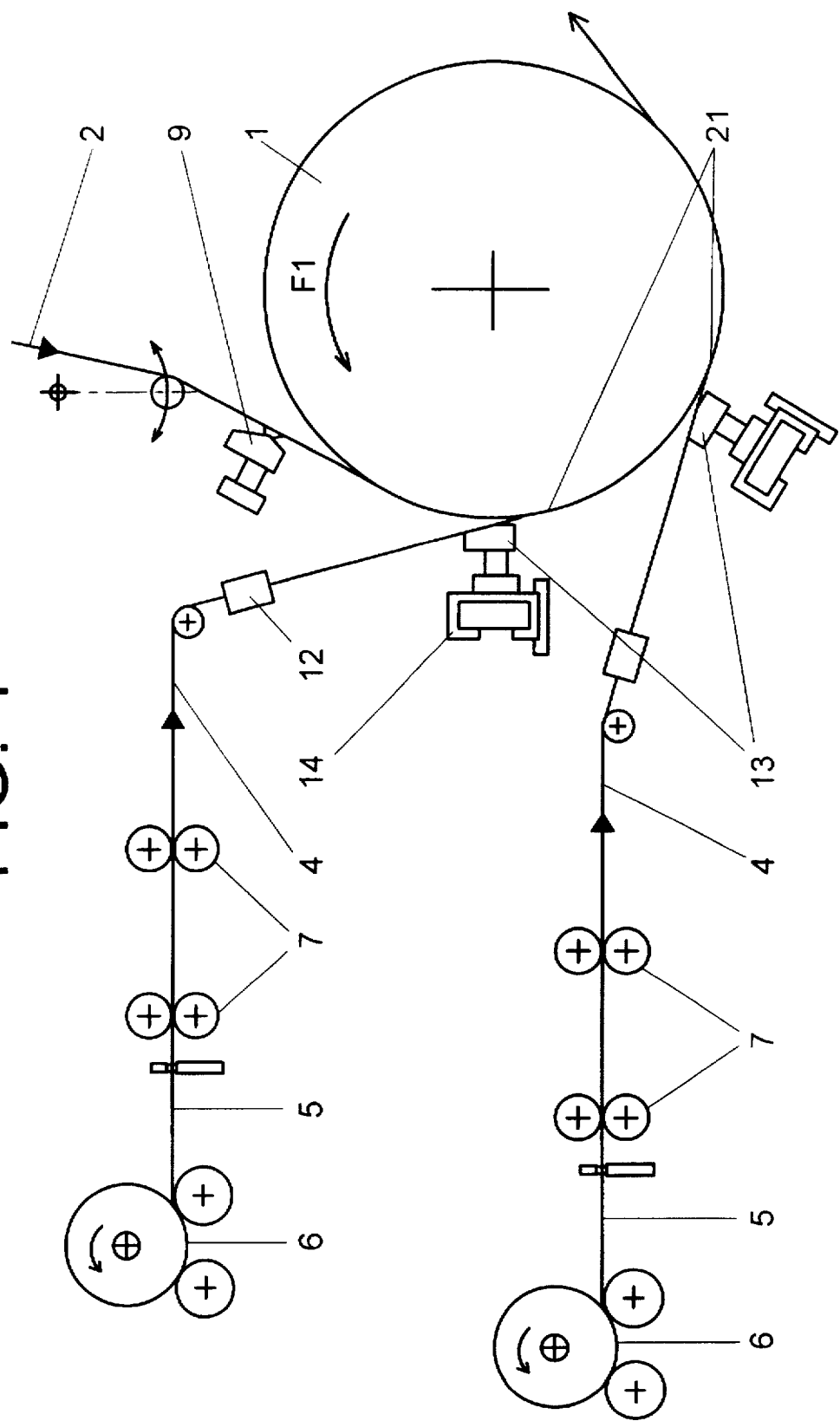
FIG. 1 is a diagrammatic side view of the main components of an apparatus for the continuous manufacture of diapers in accordance with the invention.
Figure 2:
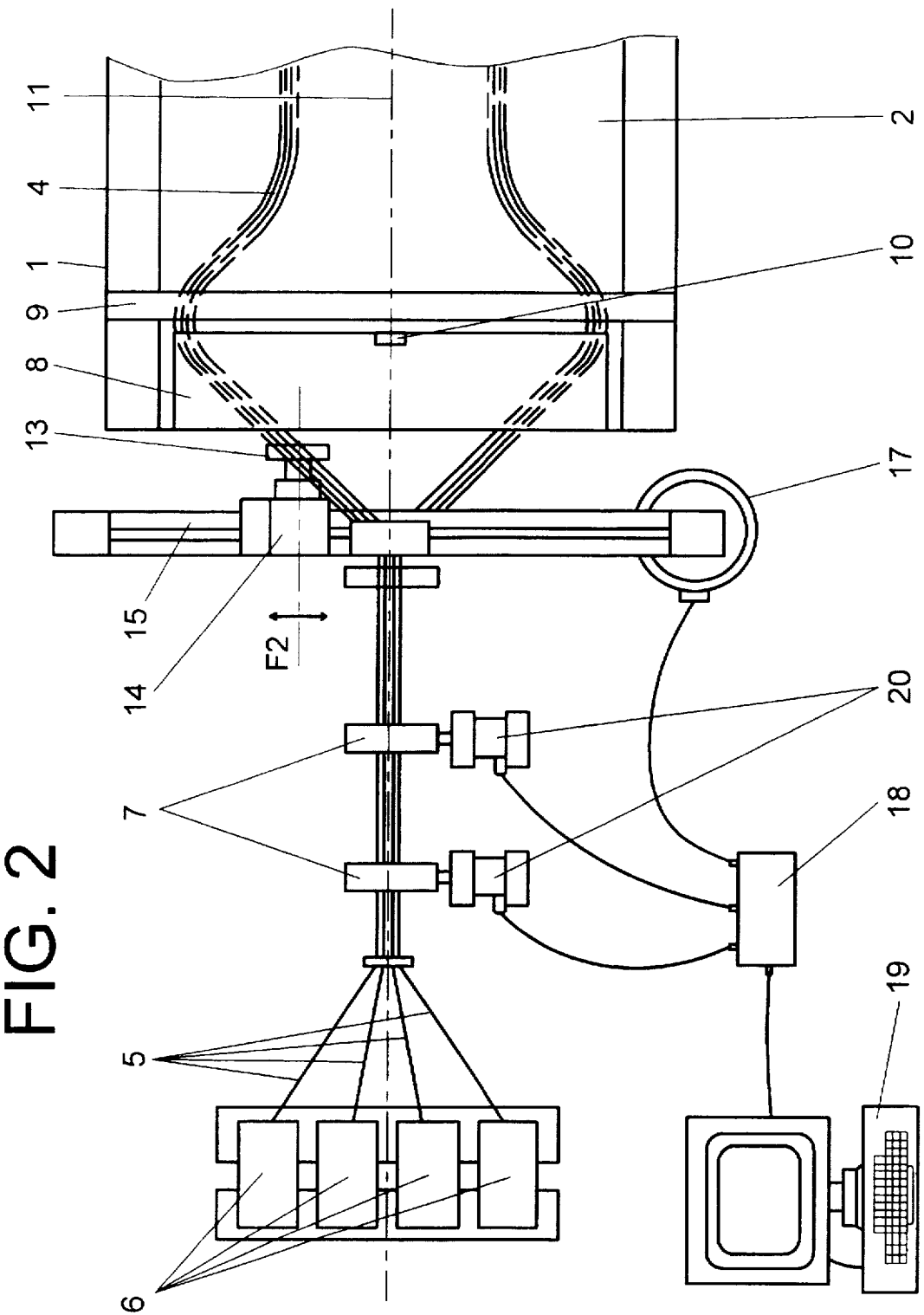
FIG. 2 is a top view of only a part of the means for feeding, tensioning and guiding the elastic members of FIG. 1.

As shown diagrammatically in FIGS. 1 and 2, the apparatus for the continuous manufacture of diapers according to the invention comprises a rotary drum 1 onto which is wound a continuous flexible sheet 2 made of a moisture-impervious heat-weldable material such as polyethylene. The drum 1 is driven in rotation in the direction of the arrow F1 so that the sheet 2 closely fits the rotary drum 1 over approximately one half of its periphery. The drum is maintained at a relatively low temperature of between 30° C. and 100° C., obtained optionally by forced artificial cooling inside the drum.

Two groups or bundles 4 of four parallel individual elastic strands 5 which may be, for example, elastic threads of a polyurethane elastomer or textured threads, such as a "LYCRA" or any other suitable elastomeric material, unwound from reels 6, are driven between two sets of tensioning rollers 7. Tensioning rollers 7 are driven in rotation so that the linear speed of travel of the elastic strands 5 leaving the tensioning rollers 7 is lower than the peripheral speed of the impervious sheet 2 on the rotary drum 1.

By appropriately adjusting the speed difference, the desired elongation for the elastic strands 5 is obtained and can be varied at regular intervals as the elastic strands move past.

An adhesive material 8 which is liquefied by melting (of hot-melt type) is delivered by a device of the nozzle type 9 for applying adhesive, which extrudes adhesive continuously over the whole width of the impervious sheet 2 as it moves past under this nozzle device 9, with the exception of a middle region 10, of small area, situated on the lengthwise axis 11 of the said sheet 2, and which is repeatedly formed according to a pitch corresponding to the length of the future diapers to be formed.

The four elastic strands 5 of each bundle 4 then run over a first stationary guiding instrument 12 and then over a guiding head 13 provided with holes or channels for guiding and holding the strands parallel to each other, and mounted so as to rotate freely with a frictionless bearing, for example of the air cushion type, on a movable trolley 14 which can slide on a slide rail 15 in the directions shown by the double arrow F2.

The trolley is driven by a rotary motor 17 or optionally by a linear motor controlled as a function of the rotation of the drum 1 and hence of the travelling position of the impervious sheet 2, by means of an electronic control unit 18, driven by a computer program run by a computer 19. This same electronic control unit allows controlling the motors 20 actuating the tensioning rollers 7.

After passing over the guiding heads 13, (only one of which is shown in FIG. 2), the elastic strands come into contact at 21 with the impervious sheet 2 on its adhesive-coated face, at the periphery of the rotary drum 1, the guiding heads being arranged in the immediate proximity of the contact point 21. Between the guiding head 13 and the contact point 21 with the impervious sheet which is at the periphery of the rotary drum 1, the elastic strands 5 are oriented in a direction tangent to the profile of the rotary drum 1.

The frictionless rotation of the guiding head 13 about an axis perpendicular to the axis of the drum 1, that is, in a plane tangent to the peripheral surface of the drum 1 in the region of the contact point 21, allows keeping the elastic strands entering the guiding head to be permanently oriented on the axis of the trajectory according to which the said strands are adhesively bonded to the impervious sheet 2, which avoids submitting the strands to high transverse forces that would be detrimental to their correct positioning and their proper adhesive bonding to the said impervious sheet 2.

The characteristics of the apparatus, in particular of the rotary drum, and the nature of the adhesive are optimized in order that an immediate bonding of the elastic strands to the impervious sheet takes place immediately after the points of contact 21, allowing the elastic strands to be bonded along a double curved outline which is symmetrical in relation to the lengthwise axis 11, as can be seen in the following figures.

Figure 3:
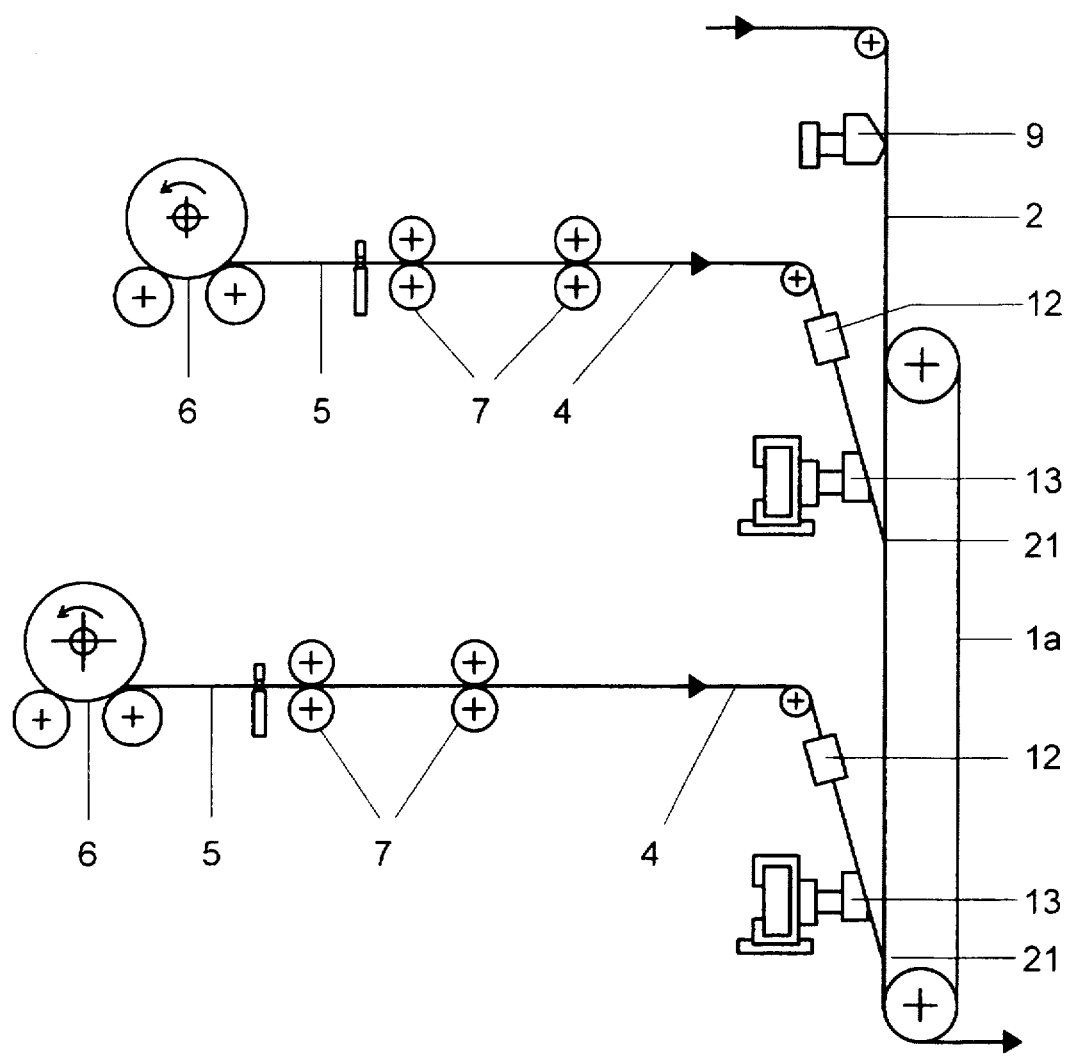
FIG. 3 is a diagrammatic side view of an alternative form of the apparatus of FIG. 1.

The apparatus according to FIG. 3 includes most of the components of the apparatus of FIG. 1, with the difference that the rotary drum 1 which is used as a supporting and driving member for the impervious sheet 2 is replaced here by a rotary endless conveyor belt 1a, said belt being preferably provided with suction capabilities for driving the sheet 2 in a flat manner.

FIG. 2 and the corresponding description also apply to the apparatus of FIG. 3, taking into account the fact that the belt 1a drives the sheet 2 with a translational motion and not with a rotary motion as does a drum.

The main advantage in using a conveyor belt 1a having suction capabilities, instead of a rotary drum, is the more accurate positioning of the elastic strands 5 of each bundle 4 on the impervious sheet 2. In fact, on a drum, the impervious sheet 2 undergoes, after application of the elastic strands under tension, a transverse retraction causing waving of the sheet, that is to say a distortion which is detrimental to the parallel positioning of the strands in the bundle. Moreover, because of the curvature of the drum surface, the distance between the various strands of a bundle varies when these strands are deposited onto the impervious sheet 2 during the transverse movements of the guiding head 13, that is to say when this head pivots about its axis of rotation. On the other hand, when the elastic strands 5 are deposited onto an impervious sheet 2 supported and driven flat by a conveyor belt 1a which applies suction, this sheet is held perfectly until the elastic strands are definitively attached and cannot therefore be distorted, and the geometrical conditions in which the deposition of the elastic strands onto the sheet 2 conveyed flat by the belt 1a takes place ensure that the distance between the strands does not vary, that is to say that the strands are parallel on the impervious sheet 2.

Figure 4:
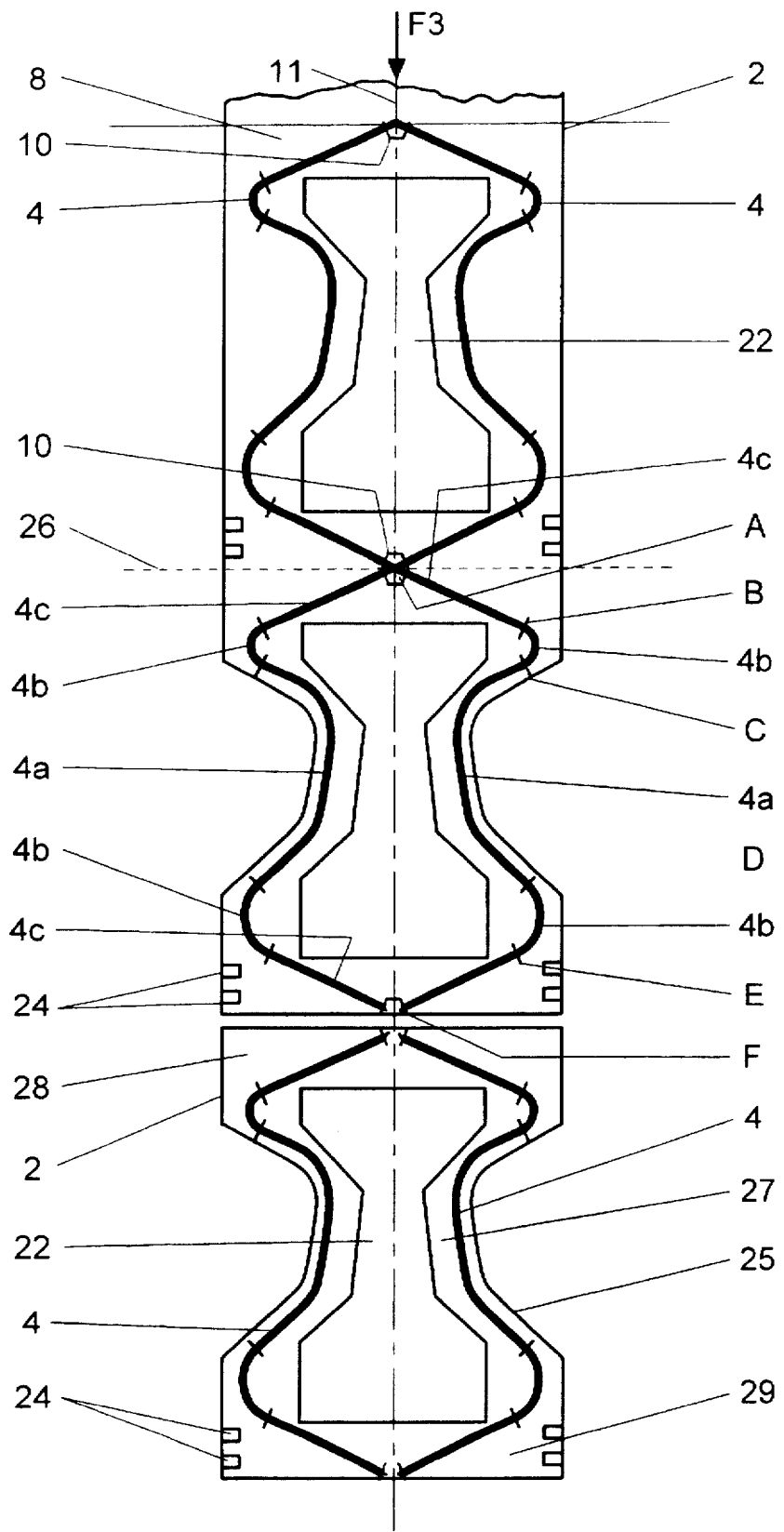
FIG. 4 is a view illustrating a number of steps of manufacture of a first embodiment of diapers according to the invention.

In a first embodiment, illustrated in FIG. 4, the continuous impervious sheet 2, which is unwound in the direction of the arrow F3 oriented along the lengthwise axis 11 of the said sheet 2, and which has received an application of adhesive 8, is provided along its two lengthwise edges with two bundles 4 of four continuous parallel individual elastic strands, shown as a single thick line for greater clarity. These two bundles cross each other at regular intervals, forming a repetitive closed outline pattern whose length along the axis 11 corresponds to that of the diapers.

The concave curved portions 4a between the points C and D, corresponding to the central crotch region of the future diapers, are adhesively bonded in the highly stretched state according to the process which has been described with reference to FIGS. 1, 2 and 3, the elongation value of the elastic strands being close to 180%, whereas the convex curved portions 4b between the points D and E, and B and C, have undergone only a very small stretching, corresponding to an elongation of approximately 5 to 10%; finally, the rectilinear portions 4c between the points A and B, and E and F, which connect the above curved portions 4b of two successive patterns, have been stretched slightly more strongly, so that the elastic strands here exhibit an elongation of approximately 50%.

It should be noted that these rectilinear portions 4c of the elastic strands cross each other in an X, in a region 10 centered on the lengthwise axis 11 of the sheet 2, and which is devoid of any adhesive material, with the result that at this emplacement, the elastic strands are not attached to the impervious sheet 2.

The deposition of absorbent pads 22, of an anatomical shape or of any other shape, and of a moisture-permeable veil 23 (which is not shown in FIG. 4 but can be seen in FIGS. 5a and 5b), which are adhesively bonded to the impervious sheet 2 using the adhesive material 8, and then of adhesive fastenings 24 on the lengthwise edges of the sheet 2, take place in a subsequent step of the process. After the step of cutting out the indentations 25, the final stage of manufacture takes place, consisting in sectioning the composite strip obtained transversely along the lines 26 so as to form the diapers like those illustrated in FIG. 5.

During the transverse sectioning the rectilinear portions 4c of the elastic strands are sectioned at their intersection, and their ends retract over a small length corresponding to the region 10 which is devoid of any adhesive material 8, that is to say as far as points A and F.

Finally, as can be seen in FIG. 5a, a diaper is obtained, in which indentations 25 in the crotch region have a concave curved outline and an inwardly running set 4 of curved elastic strands placed in a highly stretched state, the outermost strand of which is arranged close to the outline of the indentation, ensuring suitable leakproofing against the risks of transverse leakages from the absorbent pad at this spot. The two sets of elastic strands 4 extend continuously and symmetrically in relation to the lengthwise axis 11, forming an outline of practically closed perimeter around the absorbent pad 22. These two sets of elastic strands therefore make it possible both to ensure the lengthwise elasticity in the crotch region 27 and also to form, in the front 28 and rear 29 end regions of the diapers, elasticized belts which facilitate the adjustment to a user's waist and which greatly limit the risks of a leakage along the transverse edges of the diaper.

Figure 5B:
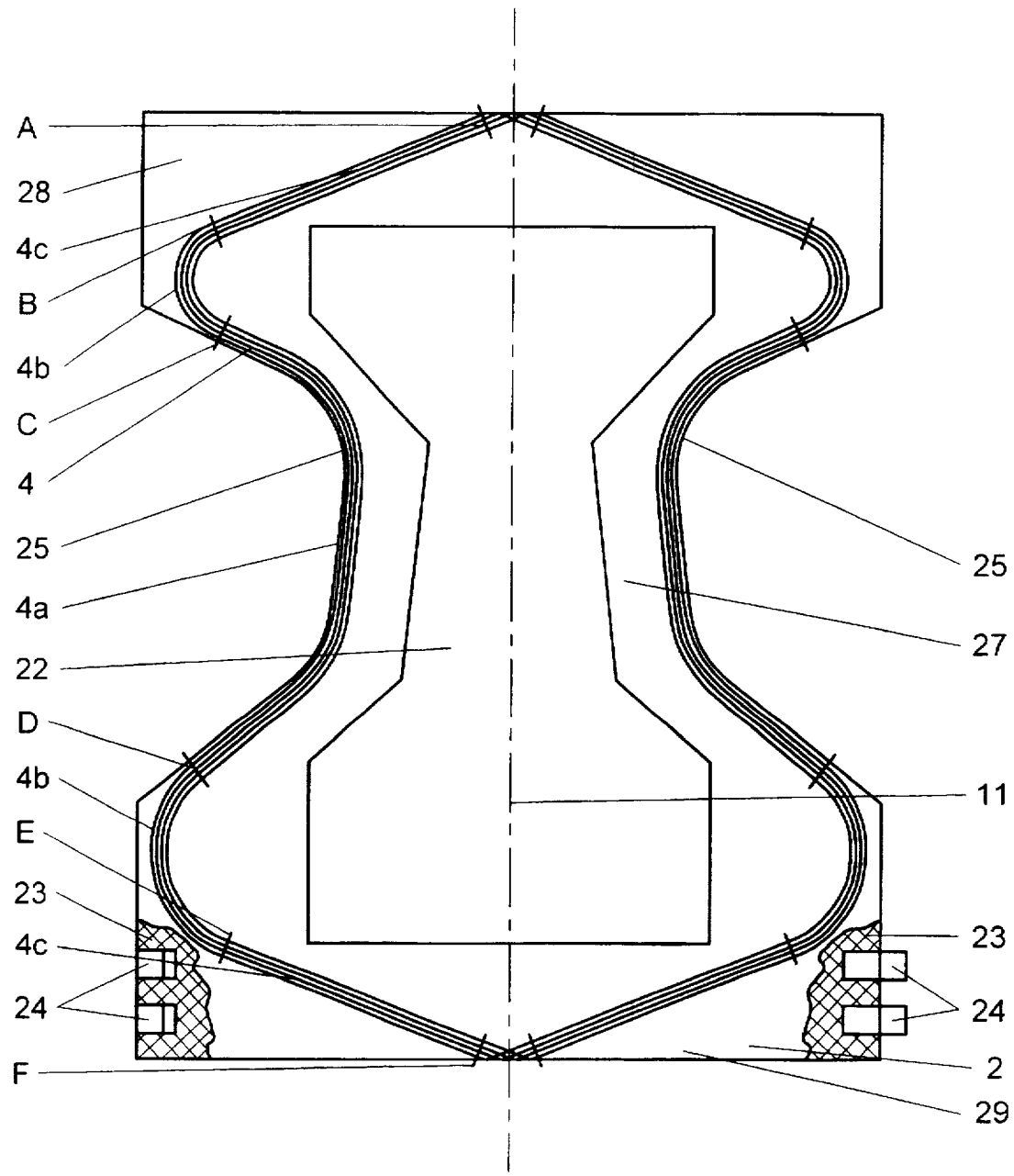
FIG. 5b is a top view, with partial cutaway, of an alternative embodiment of the diaper manufactured according to the process of FIG. 4.

Alternatively, the regions A and F the diaper may have adhesive 8 applied so that the end portions of the elastic members do not contract, but remain in contact, as illustrated in FIG. 5b, when the composite strip is sectioned to from individual diapers.

Figure 6:
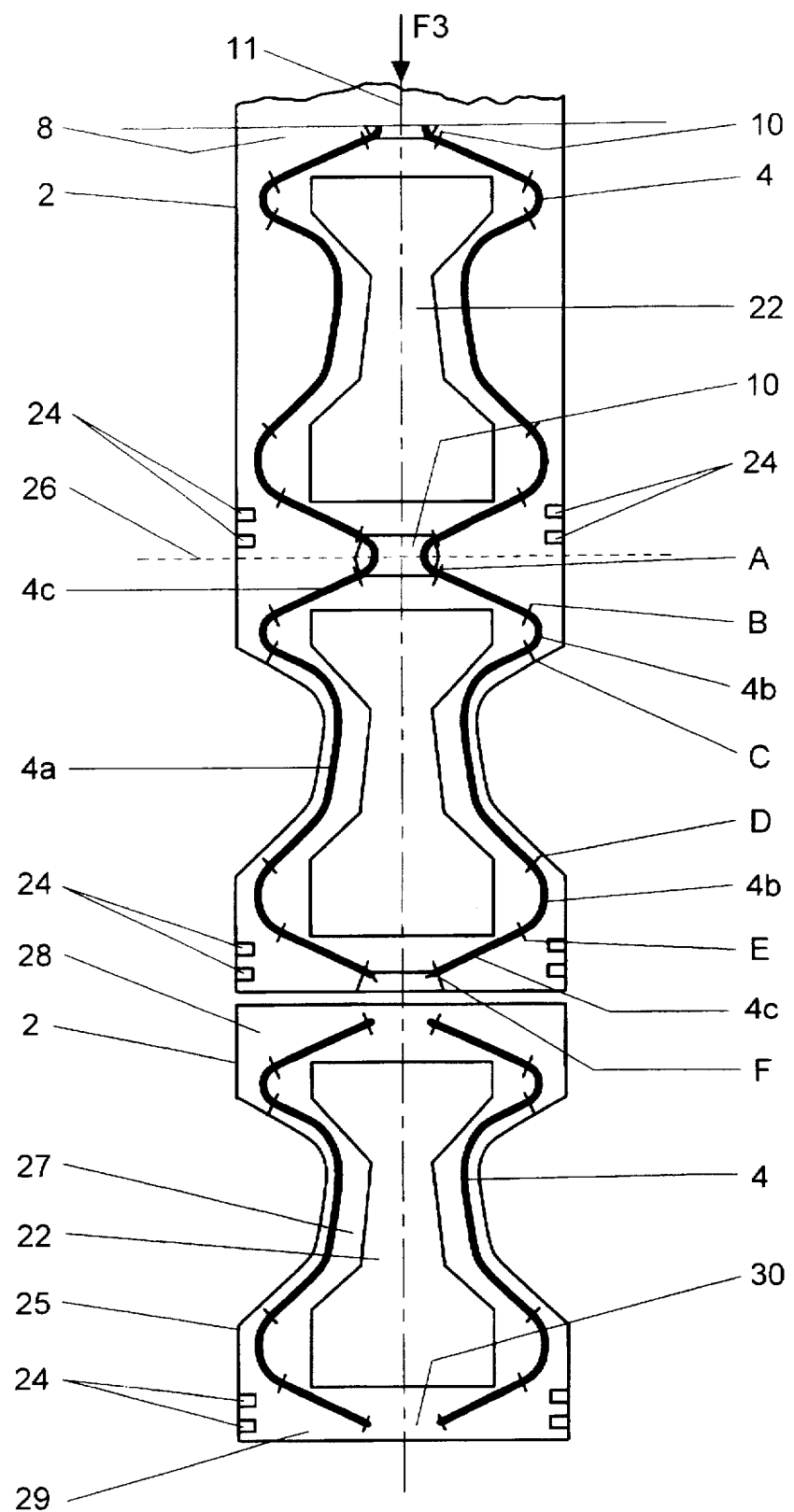
FIG. 6 is a view illustrating a number of manufacturing steps of a second embodiment of diapers according to the invention.
Figure 7:
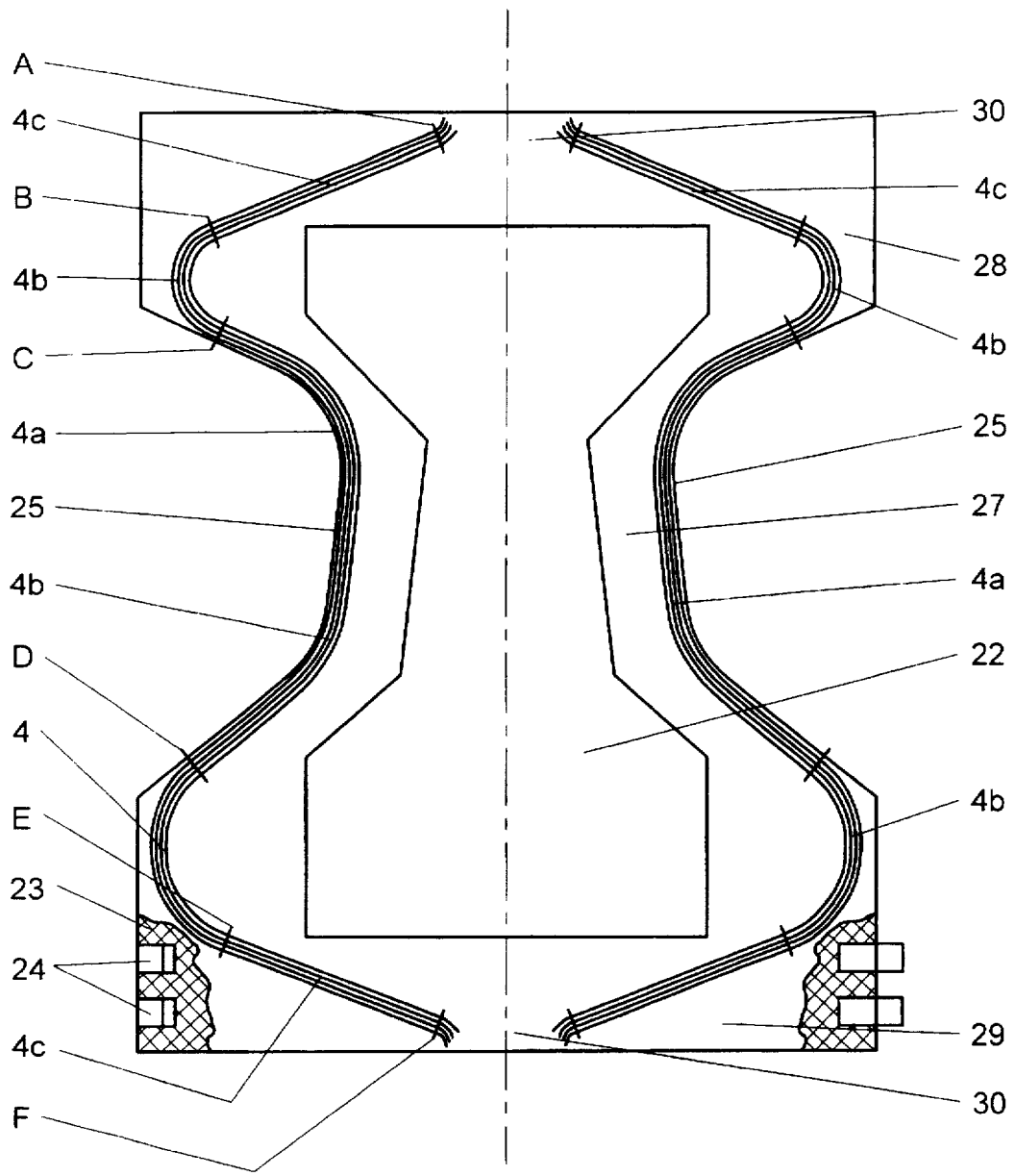
FIG. 7 is a top view, with partial cutaway, of a diaper manufactured according to FIG. 6.

In a second embodiment illustrated in FIGS. 6 and 7, where identical components bear the same references, the essential difference from the preceding embodiment lies in the fact that the two bundles 4 of continuous parallel individual elastic strands are deposited onto the impervious sheet 2 moving past in the direction of arrow F3, along its lengthwise edges, without crossing each other at regular intervals.

The rectilinear portions 4c which are symmetrical in relation to the axis 11 approach each other at point A, but then the heads guiding the two bundles 4 of elastic strands, which may, furthermore, be mounted on trolleys sliding on the same slide rail, are driven in opposite directions and the bundles 4 move apart after the points F. Between the points A and F of two successive patterns, the elastic strands which are applied onto the sheet 2 in the regions 10 which are devoid of any adhesive material will be able to retract during the step of transverse sectioning along the lines 26.

A diaper which is very similar to that of FIG. 5 is therefore obtained, as shown in FIG. 7, but in which the two sets 4 of elastic strands form an elasticized outline around the absorbent pad, the perimeter of which has, at the two ends (28 and 29) of the diaper along its lengthwise axis 11, an opening 30 whose width can be adjusted, as a function of the instructions for moving the heads guiding the elastic strands and/or the area of the adhesive-free region 10, possibly up to an extremely small value so as to approach the embodiment of FIG. 4 and 5a.

It should be noted that the "window" or adhesive-free region 10 on the impervious sheet 2 may be advantageously replaced by spraying an antiadhesive solution onto the end parts of the rectilinear portions 4c of the elastic strands, in all the envisaged embodiments.

To prevent the ends of the elastic members 4 from adhering to the impervious sheet 2, it would also be possible to keep an adhesive-free strip in the middle of the width of the impervious sheet, over the whole length of the latter, during the application 8 of the adhesive to this sheet. This would make it possible in particular to position a moisture indicator, for example by printing with a water-soluble ink, directly on the inner face of the impervious sheet.

Furthermore, although in the illustrated examples the various portions of variable tension of the elastic strands have the values indicated above, it will be understood that the invention is not limited to the use of these precise values. Moreover, it will be possible to envisage, without considerable modification, producing a continuous variation in the tension of the elastic members over the whole length of each diaper.

Finally, within the scope of the invention, the absorbent pad, instead of being of an anatomical hour-glass shape, could also be, for example, rectangular in shape, without side indentations, in which case the elastic members could follow a substantially rectilinear path over the whole crotch region.

We claim:

1. A disposable diaper comprising:

a liquid impervious outer sheet having lengthwise and transverse edges, said outer sheet having an inner face and an outer face;

a liquid-permeable inner sheet having lengthwise and transverse edges, said inner sheet having an inner face and an outer face;

a median indentation cutout in each of said lengthwise edges of said outer and inner sheets defining a narrower crotch region between two wider end regions;

an absorbent pad having lengthwise and transverse edges and having an overall dimension smaller than said inner and outer sheets disposed between said inner and outer sheets so that its lengthwise and transverse edges are set back in relation to the corresponding lengthwise and transverse edges of said inner and outer sheets, said inner and outer sheets being joined together by adhesive bonding along their edges around said pad;

fastening means for closing said two end regions around a user's waist; and elastic members secured under tension by adhesive bonding to the inner face of said outer sheet adjacent to both lengthwise edges of said absorbent pad and extending substantially over a whole length of said outer sheet, said elastic members having a higher tension in the crotch region than in the end regions, the elastic members having end portions positioned in the two end regions and transversely oriented to converge in the direction of a lengthwise center axis of said outer sheet, so that said elastic members form an elastic barrier which practically surrounds the pad and provides the outer sheet with a lengthwise elasticity in the crotch region and a transverse elasticity in the end regions, wherein said converging end portions are spaced from each other near each transverse edge of said outer sheet by a maximum distance which is less than 20% of a width of said transverse edge of said outer sheet and are inclined by at least 45° relative to the lengthwise center axis of said outer sheet.

2. A diaper according to claim 1, wherein said converging end portions are substantially rectilinear.

3. A diaper according to claim 2, wherein said converging end portions have a length such that projections of said converging end portions onto said transverse edges of said outer sheet have a length corresponding to at least 40% of the length of said transverse edges of said outer sheet.

4. A diaper according to claim 3, wherein said length of said projections corresponds to more than 50% of the length of said transverse edges of said outer sheet.

5. A diaper according to claim 1, wherein said converging end portions are inclined by at least 60° relative to the lengthwise center axis of said outer sheet.

6. A diaper according to claim 1, wherein the converging end portions are spaced from each other near each transverse edge of said outer sheet by a maximum distance which is less than 15 % of the width of said transverse edges of said outer sheet.

7. A diaper according to claim 1, wherein said converging end portions are spaced from each other near each said transverse edge of said outer sheet by a maximum distance of less than 50% of a maximum width of said absorbent pad.

8. A diaper according to claim 1, wherein said absorbent pad has two opposite indentations cut out in the lengthwise edges in said crotch region, and wherein each of said elastic members comprises a substantially rectilinear section in a median part of said crotch region connected to each converging end portion, through an outwardly concave curved section followed by an outwardly convex section, said outwardly convex section having a lower tension than the converging end portions, and said converging end portions having a lower tension than said substantially rectilinear section in said median part of the crotch region.

9. A diaper according to claim 8, wherein said substantially rectilinear sections in the crotch region have an elongation of approximately 100 to 200%, said outwardly convex sections have an elongation of approximately 5 to 10% and said converging end portions have an elongation of approximately 40 to 60%.

10. A diaper according to claim 1, wherein said elastic members are comprised of a plurality of individual parallel elastic strands.

11. A disposable diaper comprising:

a liquid impervious outer sheet having lengthwise and transverse edges, said outer sheet having an inner face and an outer face;

a liquid-permeable inner sheet having lengthwise and transverse edges, said inner sheet having an inner face and an outer face;

a median indentation cutout in each of said lengthwise edges of said outer and inner sheets defining a narrower crotch region between two wider end regions;

an absorbent pad having lengthwise and transverse edges and having an overall dimension smaller than said inner and outer sheets disposed between said inner and outer sheets so that its lengthwise and transverse edges are set back in relation to the corresponding lengthwise and transverse edges of said inner and outer sheets, said inner and outer sheets being joined together by adhesive bonding along their edges around said pad;

fastening means for closing said two end regions around a user's waist; and elastic members secured under tension by adhesive bonding to the inner face of said outer sheet adjacent to both lengthwise edges of said absorbent pad and extending substantially over a whole length of said outer sheet, said elastic members having a higher tension in the crotch region than in the end regions, the elastic members having end portions positioned in the two end regions and transversely oriented to converge in the direction of a lengthwise center axis of said outer sheet, so that said elastic members form an elastic barrier which practically surrounds the pad and provides the outer sheet with a lengthwise elasticity in the crotch region and a transverse elasticity in the end regions, wherein said converging end portions are joined to each other near each transverse edge of said outer sheet and are inclined by at least 45° relative to the lengthwise axis of said outer sheet.

12. A diaper according to claim 11, wherein said converging end portions are substantially rectilinear.

13. A diaper according to claim 12, wherein said converging end portions have a length such that projections of said converging end portions onto said transverse edges of said outer sheet have a length corresponding to at least 40% of the length of said transverse edges of said outer sheet.

14. A diaper according to claim 13, wherein said length of said projections corresponds to more than 50% of the length of said transverse edges of said outer sheet.

15. A diaper according to claim 11, wherein said converging end portions are inclined by at least 60° relative to the lengthwise center axis of said outer sheet.

16. A diaper according to claim 11, wherein said absorbent pad has two opposite indentations cut out in the lengthwise edges in said crotch region, and wherein each of said elastic members comprises a substantially rectilinear section in a median part of said crotch region connected to each converging end portion, through an outwardly concave curved section followed by an outwardly convex section, said outwardly convex section having a lower tension than the converging end portions, and said converging end portions having a lower tension than said substantially rectilinear section in said median part of the crotch region.

17. A diaper according to claim 16, wherein said substantially rectilinear sections in the crotch region have an elongation of approximately 100 to 200%, said outwardly convex sections have an elongation of approximately 5 to 10% and said converging end portions have an elongation of approximately 40 to 60%.

18. A diaper according to claim 11, wherein said elastic members are comprised of a plurality of individual parallel elastic strands.

* * * * *